United States Patent
Wang et al.

(10) Patent No.: US 9,304,669 B2
(45) Date of Patent: Apr. 5, 2016

(54) SYSTEM AND METHOD FOR DISPLAYING ANNOTATED CAPSULE IMAGES

(71) Applicant: Capso Vision, Inc., Saratoga, CA (US)

(72) Inventors: Kang-Huai Wang, Saratoga, CA (US); Gordon C. Wilson, San Francisco, CA (US)

(73) Assignee: Capso Vision Inc., Saratoga, CA (US)

( * ) Notice: Subject to any disclaimer, the term of this patent is extended or adjusted under 35 U.S.C. 154(b) by 319 days.

(21) Appl. No.: 13/864,202

(22) Filed: Apr. 16, 2013

(65) Prior Publication Data
US 2013/0311885 A1 Nov. 21, 2013

Related U.S. Application Data

(60) Provisional application No. 61/647,139, filed on May 15, 2012.

(51) Int. Cl.
| | | |
|---|---|---|
| *G06F 13/00* | (2006.01) | |
| *G06F 15/00* | (2006.01) | |
| *G06F 3/0484* | (2013.01) | |
| *G06F 17/30* | (2006.01) | |

(52) U.S. Cl.
CPC ...... *G06F 3/04845* (2013.01); *G06F 17/30876* (2013.01)

(58) Field of Classification Search
CPC . G06T 19/00; G06F 19/3406; G06F 3/04845; G06F 17/30876
USPC ................ 715/700, 762–765, 740–743, 780, 715/851–853, 719, 738, 838
See application file for complete search history.

(56) References Cited

U.S. PATENT DOCUMENTS

| | | | | |
|---|---|---|---|---|
| 2009/0074265 | A1* | 3/2009 | Huang et al. | 382/128 |
| 2010/0271468 | A1* | 10/2010 | Wang | 348/77 |

* cited by examiner

*Primary Examiner* — Kevin Nguyen
(74) *Attorney, Agent, or Firm* — Blairtech Solution LLC

(57) ABSTRACT

A method and system for displaying images captured by an in vivo imaging device are disclosed. Embodiments according to the present invention display image sequence data in a first display area. When a first annotated image is displayed in the first display area, a first thumbnail image in a second display area corresponding to the first annotated image is replaced to indicate an occurring correspondence between the first annotated image and the first thumbnail image corresponding to the first annotated image being displayed. In one embodiment, the method further comprises displaying the first thumbnail image in the second display area when one other image of the image sequence data is displayed in the first display area after the first annotated image is displayed.

30 Claims, 19 Drawing Sheets

SYSTEM AND METHOD FOR DISPLAYING ANNOTATED CAPSULE IMAGES

CROSS REFERENCE TO RELATED APPLICATIONS

The present invention claims priority to U.S. Provisional Patent Application, No. 61/647,139, filed on May 15, 2012, entitled "System and Method for Displaying Annotated Capsule Images". The U.S. Provisional Patent Application is hereby incorporated by reference in its entirety.

FIELD OF THE INVENTION

The present invention relates to diagnostic imaging inside the human body. In particular, the present invention relates to annotating images captured by a capsule camera system along with associated information.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Because of the difficulty traversing a convoluted passage, endoscopes cannot reach the majority of the small intestine and special techniques and precautions, that add cost, are required to reach the entirety of the colon. An alternative in vivo image sensor that addresses many of these problems is a capsule endoscope. A camera is housed in a swallowable capsule, along with a radio transmitter for transmitting data, primarily comprising images recorded by the digital camera, to a base-station receiver or transceiver and data recorder outside the body. Another autonomous capsule camera system with on-board data storage was disclosed in the U.S. patent application Ser. No. 11/533,304, filed on Sep. 19, 2006.

For the above in vivo devices, a large amount of image data is collected during the course of its traversing through a lumen in human body such as the gastrointestinal (GI) tract. For the autonomous capsule camera, the number of images collected may be as many as tens of thousands. The image data usually is viewed by medical professionals for diagnosis, analysis or other purposes. The image data is often displayed on a display device continuously and viewed video data at a certain frame rate, such as 30 frames per second. In order to help a viewer to navigate through the video sequence, various viewing controls such as fast forward, fast reverse, and pause are provided as part of user interface. Furthermore, annotation may be incorporated into the image data to help a physician to quickly locate images of interest. Due to the large amount of image data generated, it may take somewhere around half an hour to hours to view the video sequence. While play control and annotation may help to expedite diagnostic process, it is desirable to develop other tools to further improve the viewing experience.

BRIEF SUMMARY OF THE INVENTION

A method and system for displaying images captured by an in vivo imaging device are disclosed. Embodiments according to the present invention display image sequence data in a first display area. When a first annotated image is displayed in the first display area, a first thumbnail image in a second display area corresponding to the first annotated image is replaced to indicate an occurring correspondence between the first annotated image and the first thumbnail image corresponding to the first annotated image being displayed. An embodiment according to the present invention may further comprise displaying the first thumbnail image in the second display area when one other image of the image sequence data is displayed in the first display area after the first annotated image is displayed. The annotation information associated with the annotated images can also be displayed. A timeline associated with the image sequence data can be displayed, wherein markers are shown on the timeline to indicate locations of the annotated images.

In one embodiment, the first thumbnail image in the second display area is replaced by a blank space or a NULL space. The first thumbnail image in the second display area may be replaced by a token and the token may correspond to a representative icon or image information associated with the first annotated image being displayed. The image information may correspond to annotation information, frame information, time information, or any combination thereof. The first thumbnail image in the second display area may be replaced for more than one frame period.

A method for annotating images captured with an in vivo imaging device is disclosed. Embodiments according to the present invention comprise selecting at least one image to be annotated from the image sequence; accepting annotation information from a user for said at least one image to generate annotated images; and generating thumbnail images corresponding to the annotated images, wherein a confirmation is provided for each thumbnail image generated, and wherein a first thumbnail image corresponding to a first annotated image is displayed in a second display area and the first annotated image is blanked from the first display area.

DETAILED DESCRIPTION OF THE INVENTION

Figure 1A:
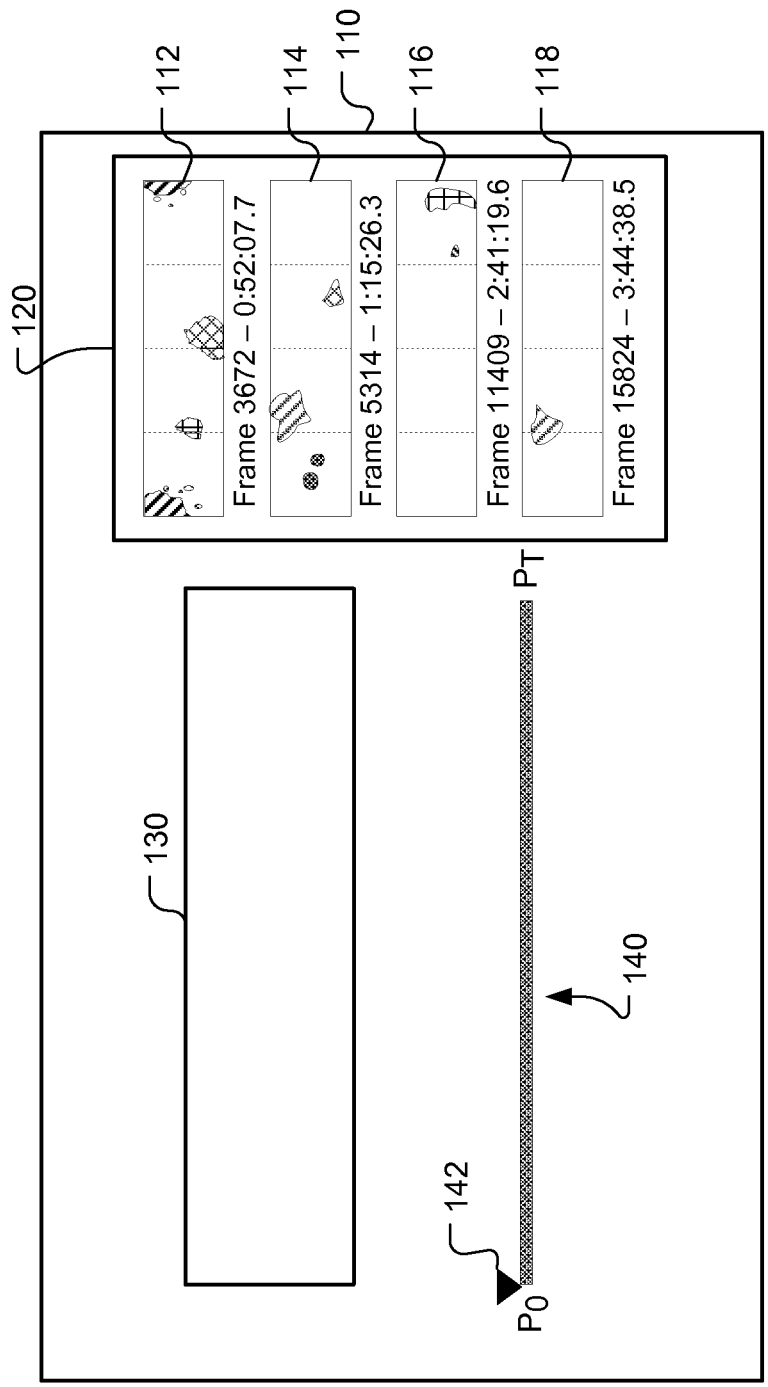
FIG. 1A illustrates an example of displaying annotated image sequence with thumbnail images and a timeline.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. Reference throughout this specification to "one embodiment," "an embodiment," or similar language means that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

A capsule camera travels through the GI tract and exits from the human body via the anus. During the course of travelling through the GI tract, the capsule camera will capture a large amount of images, which can be stored in an on-chip memory or transmitted to a base station through wireless link. The retrieved or received images are usually transferred to a base station for processing or viewing. The accuracy as well as efficiency of diagnosis is important. A health-care professional may prepare the captured images by adding annotations to identify an image or images of interest. The annotation is also called a bookmark in this disclosure. The bookmark usually is used to indicate an image or images that contain characteristics or features that are useful for viewing, diagnosis or analysis. For example, a bookmark may be used to indicate an image or images that depict the transition from one part of the GI tract to another part, such as the transition from cecum to ascending colon. A bookmark may be used to indicate an image or images that depict pathologic characteristics in the GI tract. A bookmark may also be used to divide the image sequence into multiple sections to allow quick access to any of the sections for viewing. The annotations may be stored along with the data of captured images or stored separately.

The annotated images serve as a useful tool for a medical professional to examine the image sequence and quickly identify anomalies in the GI track. An embodiment according to the present invention uses one part of the display area for displaying the image sequence and another part of the display area for displaying multiple annotated images associated with the image sequence in reduced resolution, i.e., thumbnail images. For example, in FIG. 1A, first display area 130 on display device 110 can be designated to display the image sequence. Second display area 120 on display device 110 is designated to display multiple thumbnail images. The information regarding the locations of the thumbnail images in the sequence is useful. Accordingly a timeline marked with locations of the thumbnail images can be optionally displayed with the image sequence and the thumbnail images. The timeline along with user interface may be used as a navigation bar. For example, navigation bar 140 is displayed below display area 130. In the example of FIG. 1A, four annotated images are associated with the sequence. Accordingly, four thumbnail images 112, 114, 116, and 118 are displayed in display area 120 as shown in FIG. 1A. A marker (142) associated with the location of a currently displayed image can be provided to a user. This marker can also be moved around in the timeline by the user to navigate through the image sequence. For example, a user may use a pointing device and a cursor displayed on the display device to move the marker. Furthermore, the number and/or corresponding time and/or estimated location in the body associated with each thumbnail image can be optionally displayed. A display window to show the frame number and/or associated time code can be used to provide location information of the current image within the sequence.

Figure 1B:
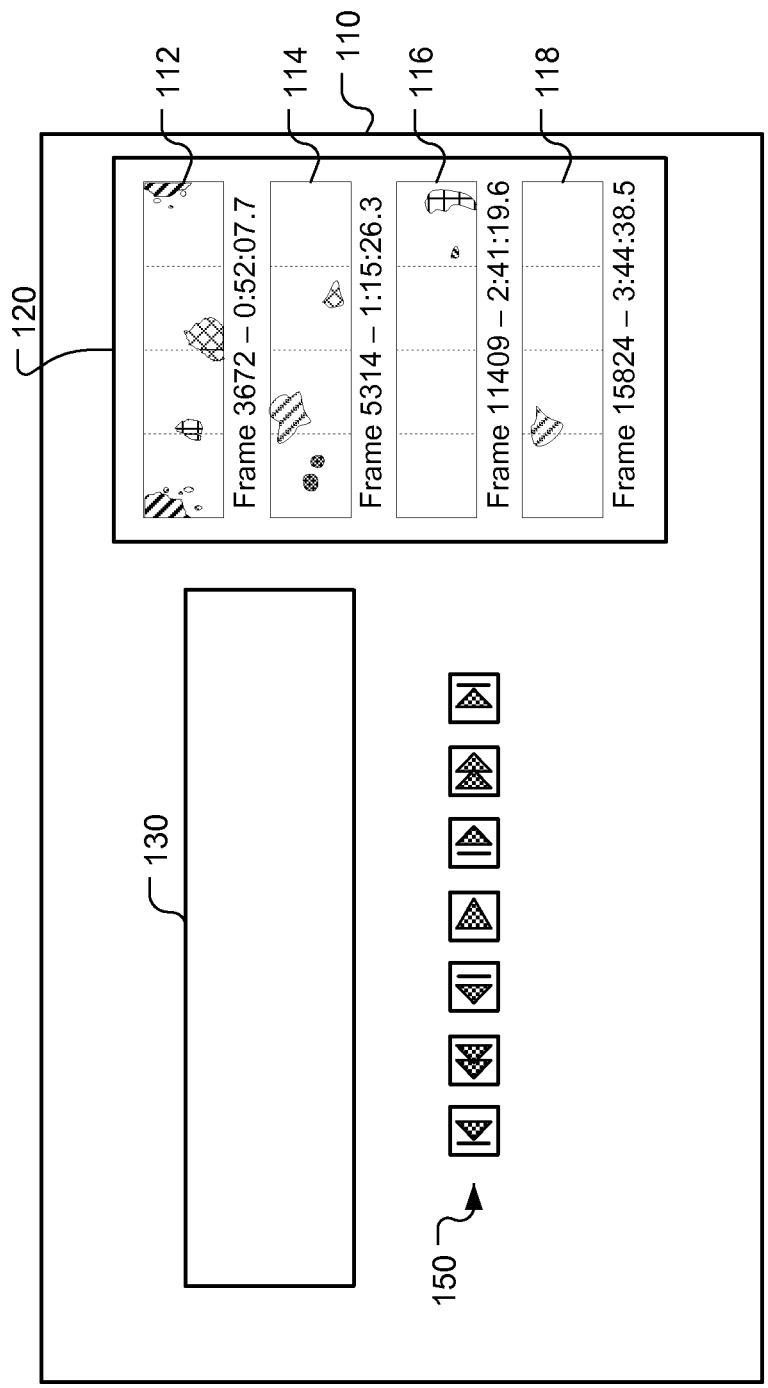
FIG. 1B illustrates an example of displaying annotated image sequence with thumbnail images and graphical user interface (GUI)-based playback control.

Besides using the navigation bar, graphic user interface (GUI) 150 can be displayed to allow actions such as Play/Pause, Next Frame, Previous Frame, Fast Forward, Reverse, Move-to-Beginning and Move-to-End as shown in FIG. 1B. When an annotated image in the image sequence is displayed, the corresponding thumbnail image can be changed momentarily to indicate the occurring correspondence between a currently displayed annotated image and a thumbnail image. A user may take advantage of this feature to quickly spot images of interest. For example, when a thumbnail image is changed momentarily, the user may pause the video display and use the Single Frame mode (i.e., Next Frame and Previous Frame) to search around the paused position for images of interest. In addition, Slow Forward or Slow Reverse may also be provided as additional play control for convenience. When the GUI based play control is used, the timeline 140 can still be displayed optionally to indicate the location of an image being currently displayed.

When the image sequence is displayed in display window 130, it will be useful to alert a viewer that an occurring correspondence between a current image being displayed and a thumbnail image in second display area 120 occurred. Upon the alert, the viewer may pay close attention to the corresponding annotated image and/or images in the neighborhood of the corresponding annotated image. Normally when a thumbnail image is created with annotation, it corresponds to a pathological, physiological or procedural point of interest. A doctor may view a range of images in the sequence and then come back to view it again. The thumbnail images to the image sequence are like bookmarks to a book. A reader may add bookmarks to indicate pages of interest or importance while reading the book so that the reader can jump easily and quickly to pages where the reader marked as interesting or important in the book. Similarly, a doctor may like to create thumbnail images during viewing of the image sequence to indicate these points of interest. When the doctor needs to view the image sequence again in another sitting or in another time, the indication of the occurring correspondence between the image being displayed in the main display area 130 and one of the thumbnail images in the second display area 120 will save the doctor time by not initiating unnecessary thumbnail image creation and then being frustrated after realizing he/she has done it before. In another situation, the video might be reviewed by a different doctor. The indication of correspondence will provide quick confirmation to the reader that this finding has been marked and no need to annotate again. This indication of correspondence could be done by momentarily changing the display of the corresponding thumbnail image. This momentary change in the display of the corresponding thumbnail image can cause a visual alert for the viewer. The change in display of the corresponding thumbnail image may be achieved by momentarily displaying an empty place or other types of place holder, any icon or symbol, or text information (e.g., the time code of the corresponding procedure). When the alternative display (i.e., the empty place or other types of place holder, any icon or symbol, or text information) is different from the regular thumbnail image, the effect of visual alert can be generated. In the field of endoscopy, it takes a long time and high cost to train an endoscopist. Therefore, a trained endoscopist is a precious societal asset. Reduction in required viewing time or examination time means more patient serving capability, i.e., less waiting days for patient and/or reduced healthcare cost. Therefore, the feature of indicating correspondences between image sequence and thumbnail images provides a convenient workflow and streamlines the review process. It also addresses the aspect of dynamic economy of endoscopy video reviewing by doctors.

Figure 1C:
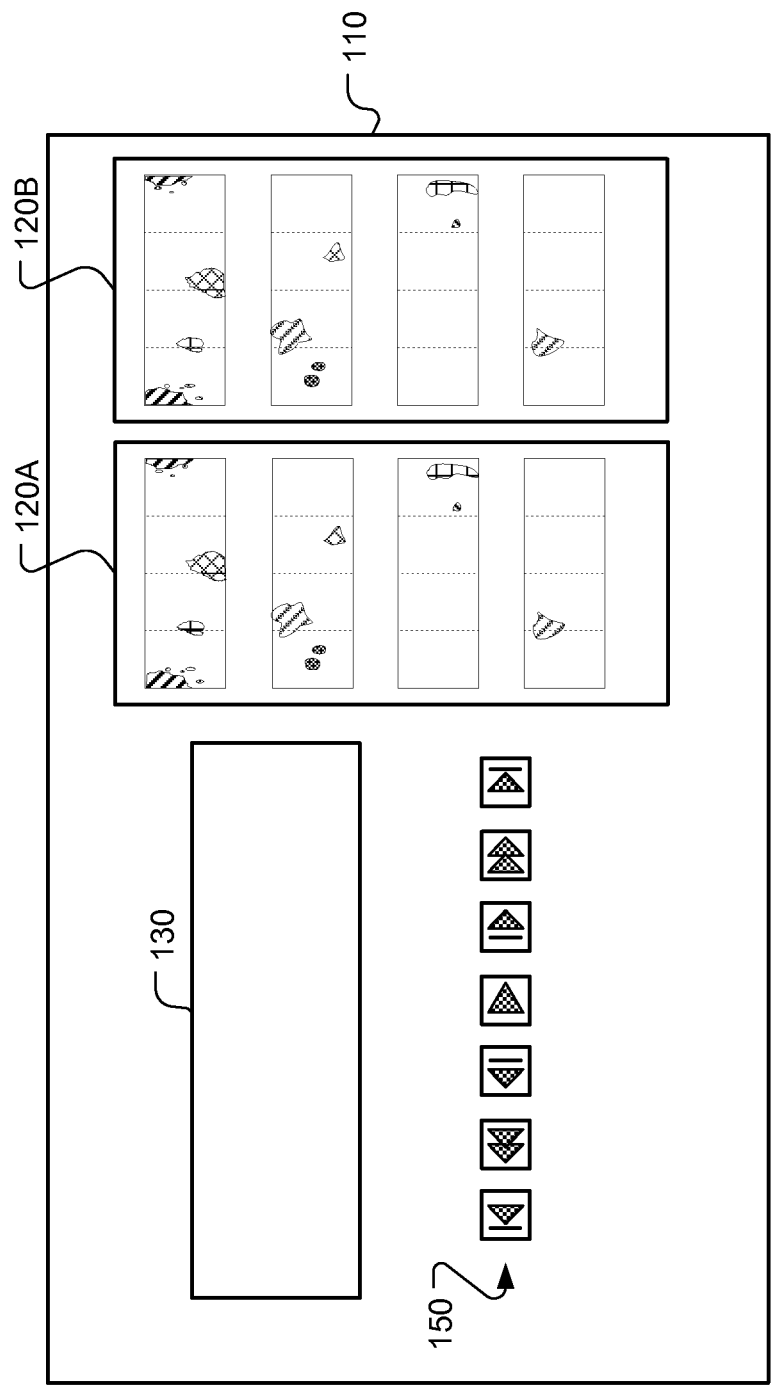
FIG. 1C illustrates another example of displaying annotated image sequence with thumbnail images, where two display areas are provided for two set of thumbnail images.

To address a more complex situation, a second set of thumbnail images can be created according to another embodiment of the present invention. For some more complex pathological or physiological point of interest where different doctors may have different opinions, a second set of thumbnail images can be created with their own annotation separately. This is in contrast to the situation where two doctors edit the corresponding annotation based on one set of thumbnail images. These two sets of thumbnail images can be displayed in the thumbnail display area (120A and 120B). FIG. 1C illustrates an example of capsule display with thumbnail/annotation, where two annotation/thumbnail display areas 120A and 120B are provided. While the same thumbnail images are shown in these two annotation/thumbnail display areas of FIG. 1C, the two sets of thumbnail images can be different. The number of thumbnail images generated may be different for the two annotation/thumbnail display areas. In one embodiment, there is an attribute to show that two sets of thumbnail images are generated by different doctors or by one doctor at different times. For example, the color of the time code under the thumbnail image can be different. The border of the thumbnail image can use a different color. Different icons or symbols may also be used to indicate different doctors. In one embodiment, the attribute option can be selected by the reviewer so that thumbnail images associated with one doctor are shown with different attribute from those associated with a different doctor. In another embodiment, thumbnail region 120 only shows thumbnail images associated with particular attribute options. For example, the attribute option can be configured so that only thumbnail images associated with a selected doctor will be displayed in thumbnail region 120.

Figure 2A:
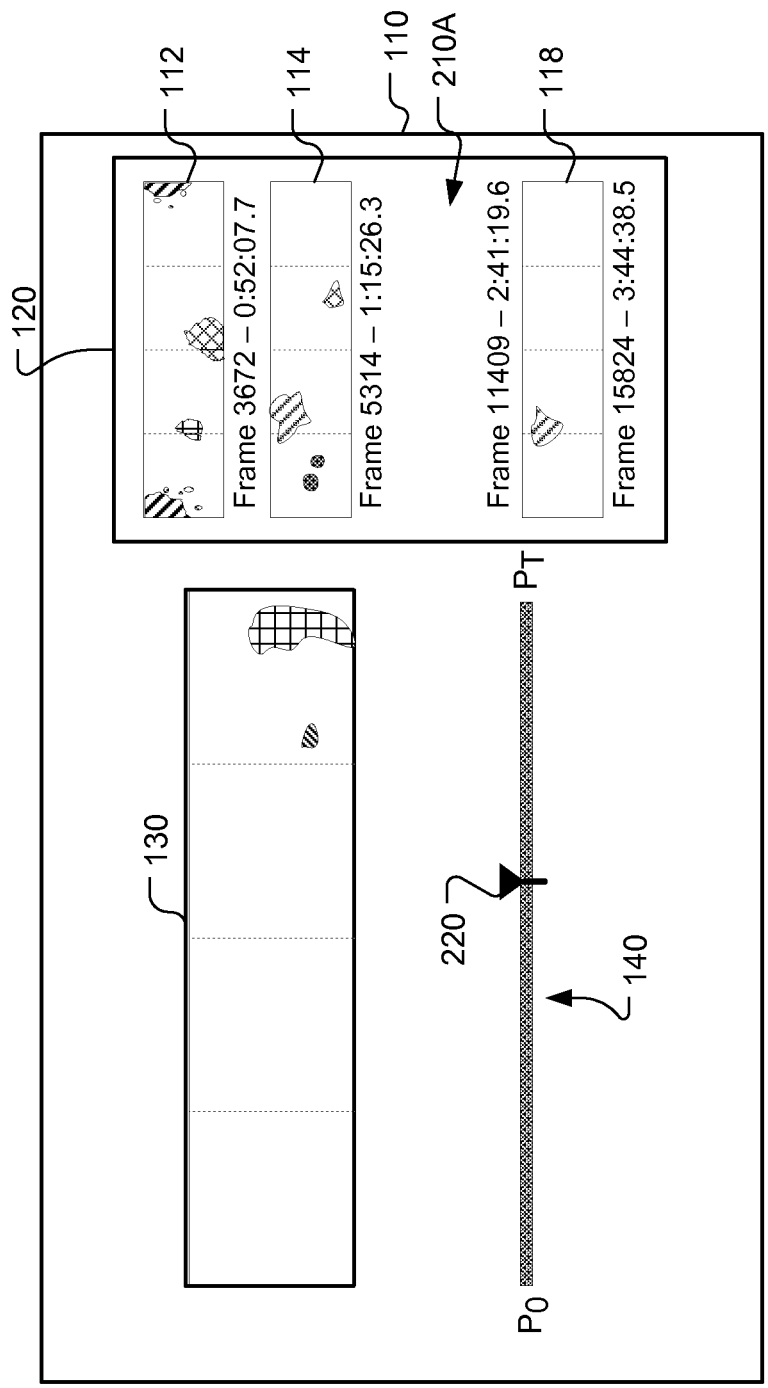
FIG. 2A illustrates an example of displaying annotated image sequence according to the present invention, where the thumbnail image corresponding to an annotated image is omitted when the corresponding annotated image is displayed.

An image sequence along with annotated images can be loaded to a viewing station for a doctor to examine. The corresponding thumbnail images can be retrieved or derived from the annotated images. The frame number and/or corresponding time associated with each thumbnail image can be read back or determined from the database for the image sequence. The thumbnail images along with the optional frame numbers and/or corresponding times can be displayed. Display area 130 for the image sequence may be left blank initially or the first image of the image sequence can be displayed. When a video (i.e., image sequence) is displayed, the display progress may be indicated on the timeline. As mentioned before, an occurring correspondence between an image being displayed and an annotated image can be indicated by momentarily changing the display of the corresponding thumbnail image. When the image sequence is displayed at a video display rate, such as 30 frames per second, a momentary change lasting for one frame period may be hard to notice. In order to enhance the visual alert by momentarily changing the display, the period of time for momentarily changing the display may be extended to more than one frame time. For example, when an occurring correspondence between a currently displayed image and a thumbnail image occurs, the currently displayed image may be repeated multiple frame times while the corresponding thumbnail image is also changed (such as replaced by a block area, a highlighted solid color, or a flashing color) multiple frame times. FIG. 2A illustrates an embodiment according to the present invention, where the video is played to a location corresponding to an annotated image with a corresponding thumbnail image 116. In FIG. 2A, blank image 210A is used to replace thumbnail image 116 as a means to indicate when the corresponding thumbnail image is displayed in the main display area (130). At the next time frame, the display of thumbnail image 116 in display area 120 will resume. This momentary change associated with thumbnail image 116 in display area 120 will cause a visual alert to indicate the occurring correspondence between an annotated image being displayed and its corresponding thumbnail image. The display of blank space 210A may be extended for multiple-frame time to enhance the visual alert. A doctor may also view the image sequence by selecting a corresponding thumbnail image. For example, thumbnail image 116 may be selected as shown in FIG. 2A and the corresponding annotated image is displayed in display area 130. Thumbnail image 116 in display area 120 is replaced by blank space 210A when the corresponding annotated image is display in display area 130 according to an embodiment of the present invention. The change in displaying the corresponding thumbnail image provides an indication of occurring correspondence between the annotated image and the corresponding thumbnail image. In addition, it also provides a confirmation or acknowledgement for accepting the thumbnail image selected by the doctor. After a thumbnail image is selected, the doctor may examine this annotated image or neighboring images of this annotated image. The doctor may use playback control to navigate around the image sequence. Again, if an annotated image is being displayed, an occurring correspondence between this annotated image and a corresponding thumbnail image will be indicated by a display change of the corresponding thumbnail image to alert a viewer. Pointer 220 in FIG. 2A can also be used to indicate the current display location when timeline bar 140 is used.

Figure 2B:
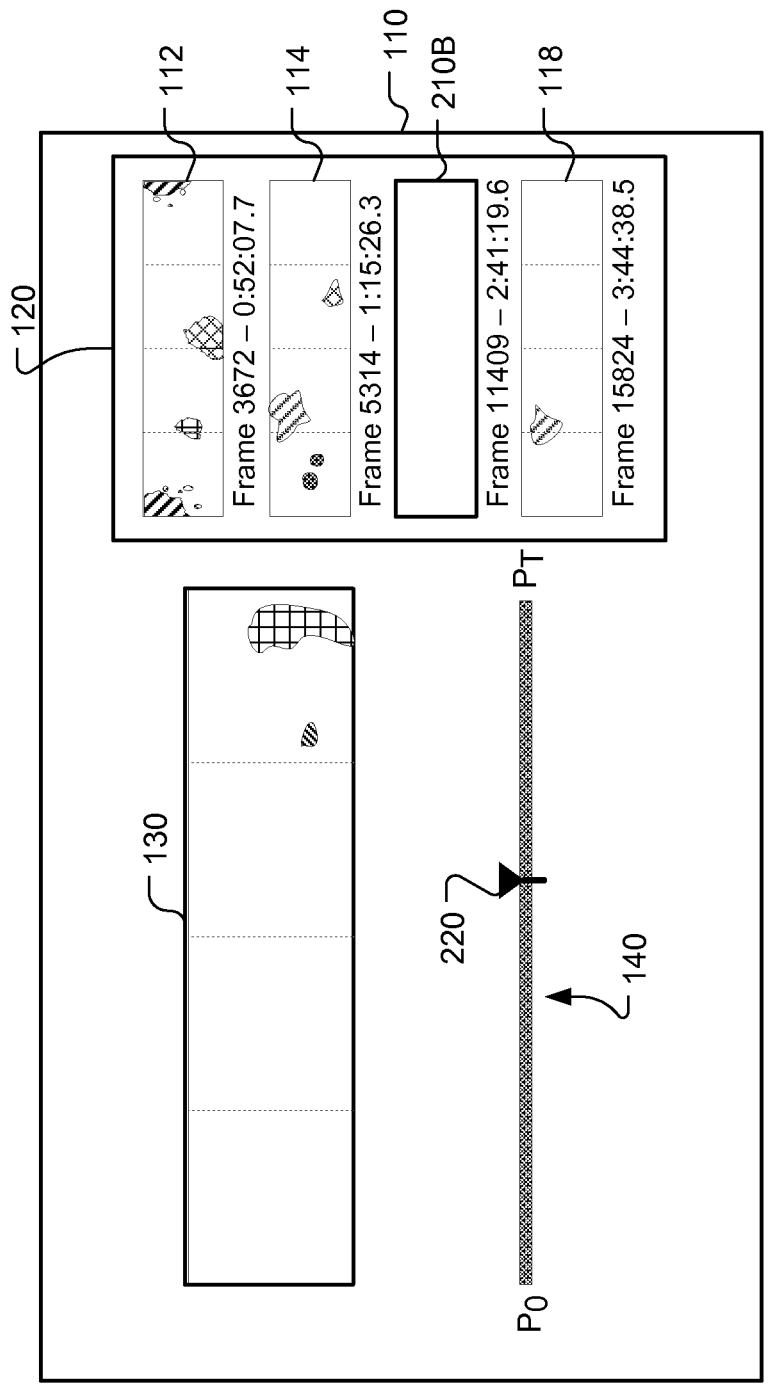
FIG. 2B illustrates an example of displaying annotated image sequence according to the present invention, where the thumbnail image corresponding to an annotated image is replaced by a box when the corresponding annotated image is displayed.
Figure 2C:
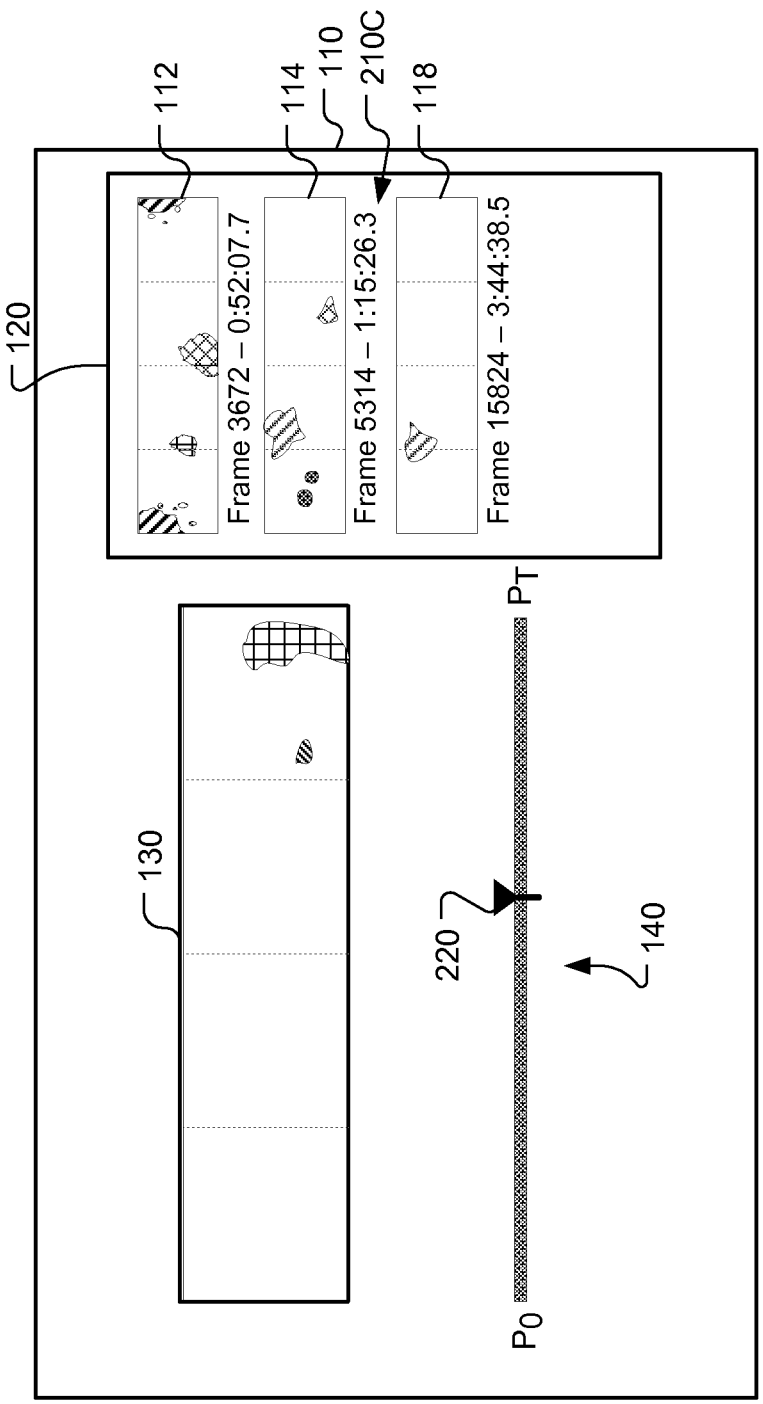
FIG. 2C illustrates an example of displaying annotated image sequence according to the present invention, where the thumbnail image corresponding to an annotated image is removed and the following thumbnail images are moved up when the corresponding annotated image is displayed.
Figure 2D:
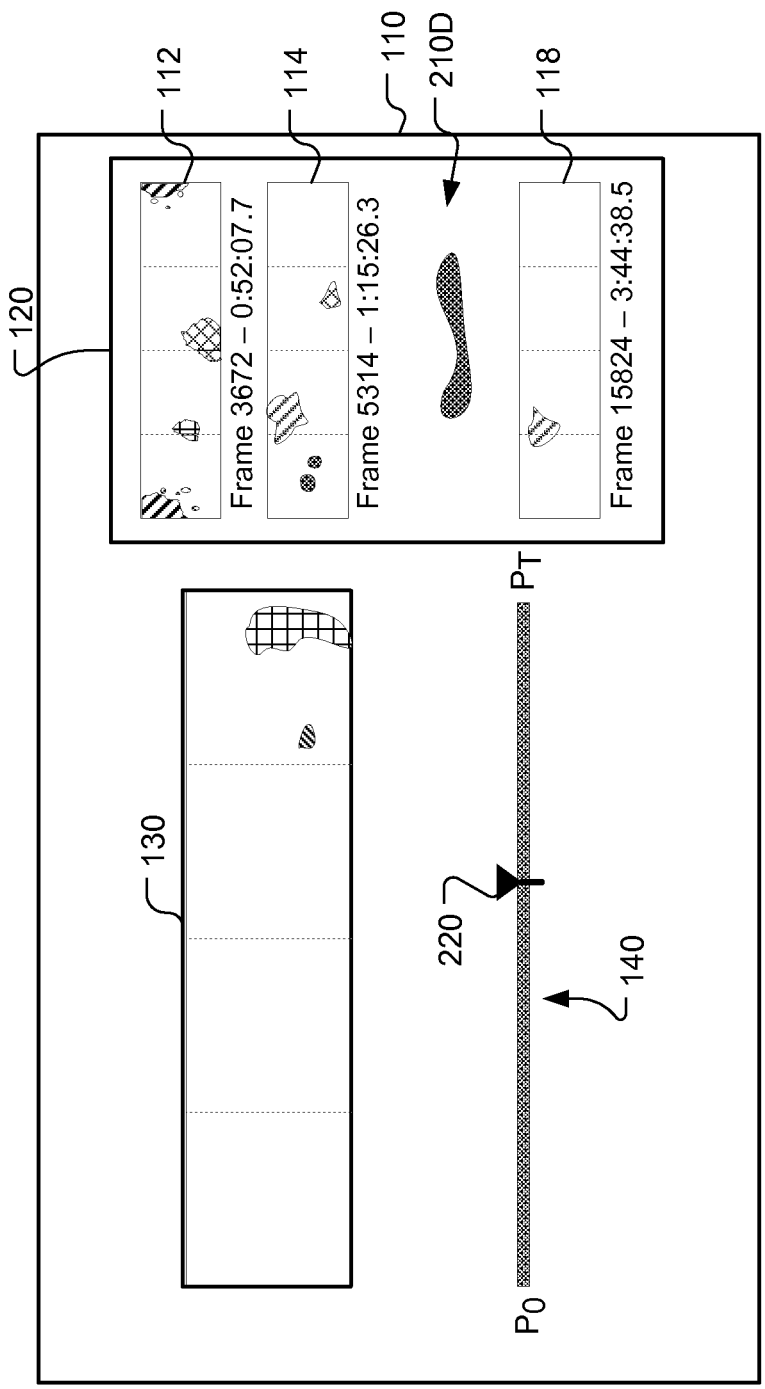
FIG. 2D illustrates an example of displaying annotated image sequence according to the present invention, where the area for the thumbnail image corresponding to an annotated image is replaced by a token when the corresponding annotated image is displayed.
Figure 2E:
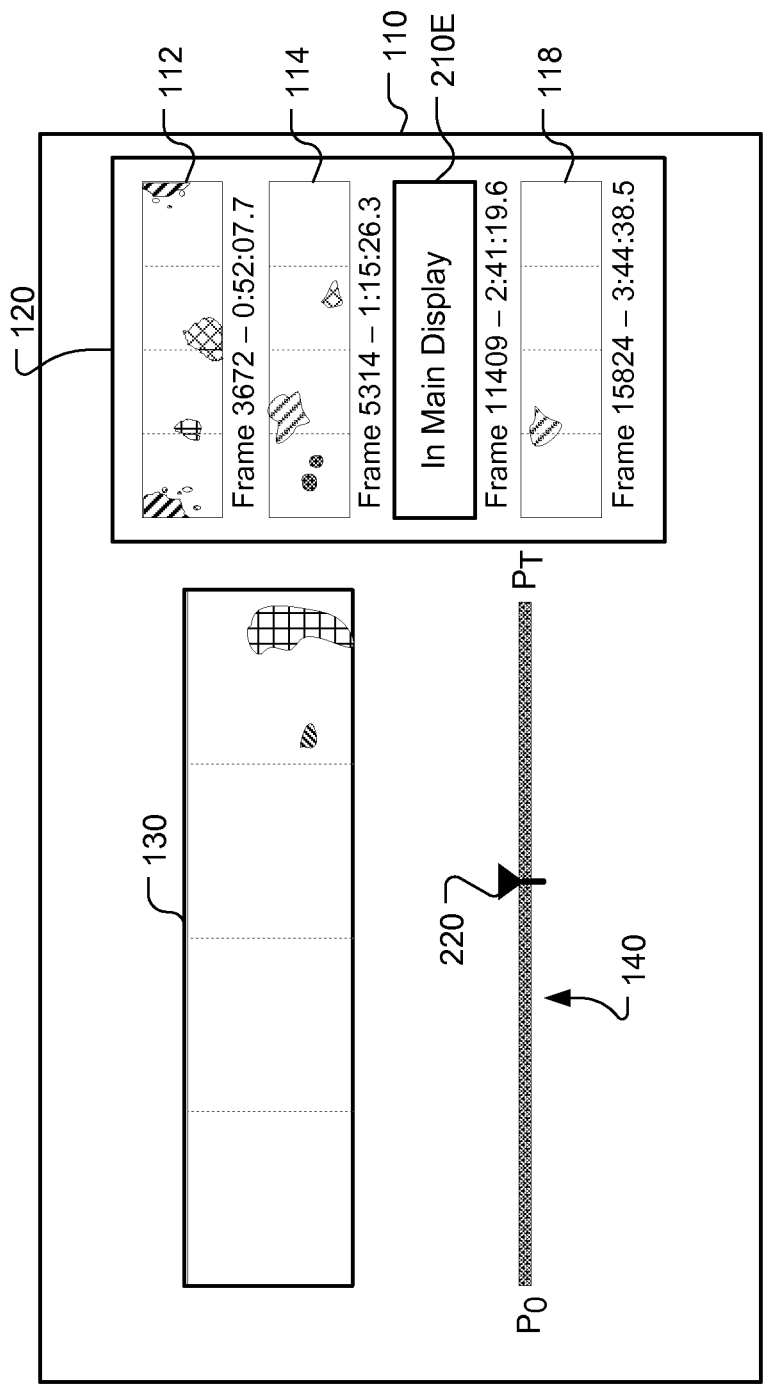
FIG. 2E illustrates an example of displaying annotated image sequence according to the present invention, where a text message is displayed in the area for the thumbnail image corresponding to an annotated image to inform a viewer that the corresponding annotated image is displayed.

While the area for the corresponding thumbnail image can be left blank (i.e., replaced by a blank space), a box 210B can be alternatively displayed at the position corresponding to thumbnail image 116 as shown in FIG. 2B. When the thumbnail image 116 corresponding to an annotated image being displayed is omitted, area 210C for the corresponding thumbnail image can be removed by shifting the remaining thumbnail images up to fill the blank area as shown in FIG. 2C. After the corresponding annotated image is displayed, the associated thumbnail image can be put back in the thumbnail display area. While the blank area is replaced by a box as shown in FIG. 2B, any token or symbol can be displayed in the area. The token or symbol may be any information associated with the annotated image being displayed, such as the annotation information, frame information, time information, or a representative icon. The representative icon may correspond to the part of the GI track that the annotated image is located, such as cecum, ileum and etc. For example, an icon 210D is shown in FIG. 2D. The token may also be a symbol to fill the area which may not contain any information related to the annotated image. For example, box 210B is an example of a symbol. The symbol may have a very bright color to make visual alert more noticeable. In another embodiment of the present invention, text information is displayed at the position corresponding to thumbnail image 116 as shown in FIG. 2E. The text information may contain image specific information such as the part of the GI track that the annotated image is located (e.g., cecum, ileum and etc.). The text information may also provide just provide general information such as "In Main Display" to inform a user that the thumbnail image is being shown in the main display.

In the examples shown in FIG. 2A through FIG. 2E, the thumbnail image corresponding to an annotated image is replaced by an empty space or a token (such as a symbol or an outline box) or the vacated space is filled by another thumbnail image. However, any other change applied to the corresponding thumbnail image will serve the purpose of visual alert to indicate the occurring correspondence between the annotated image being display and a corresponding thumbnail image. For example, the thumbnail image may be highlighted with an outline box, a graphic overlay with solid color or partial transparency. Furthermore, a combination of alerting means illustrates in FIG. 2A to FIG. 2E can be used. For example, the text message "In Main Display" can be a graphic overlay on top of a colored box.

Figure 3A:
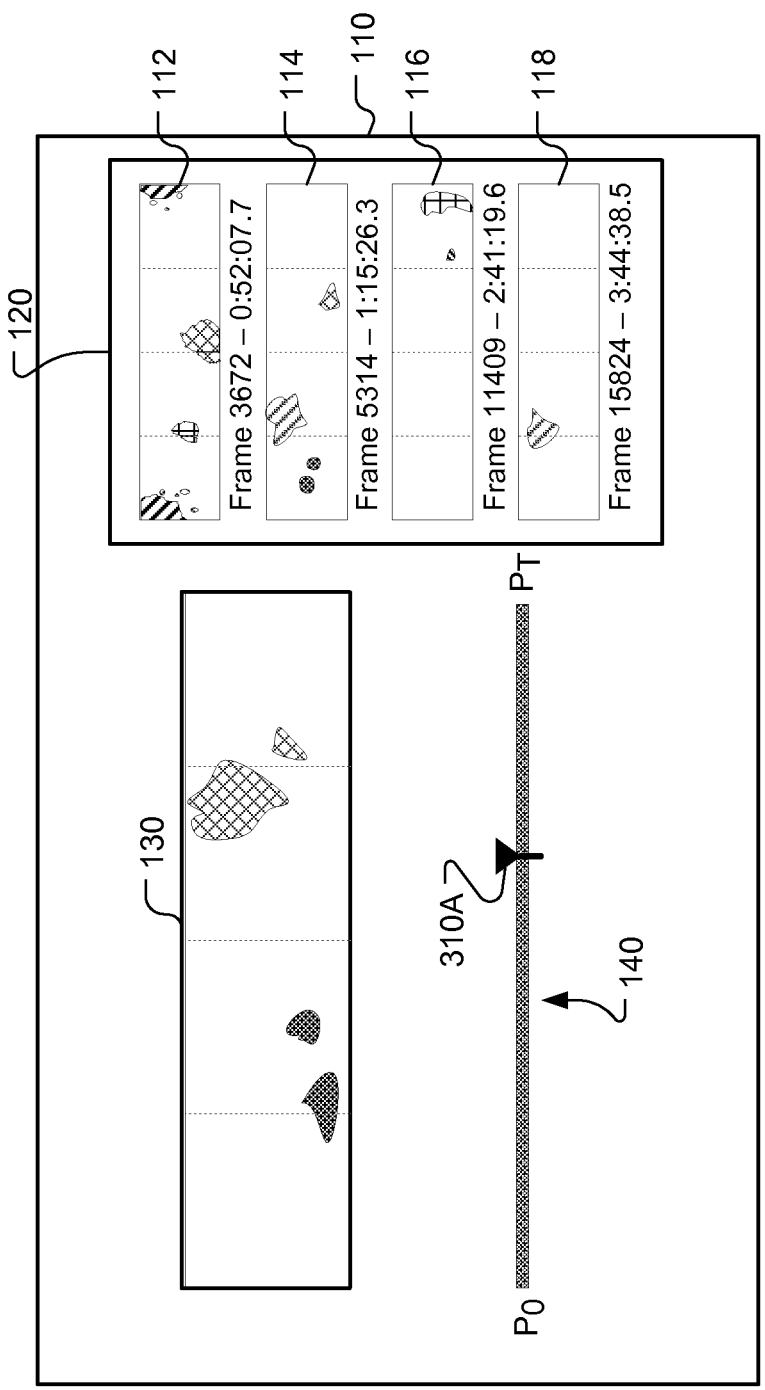
FIG. 3A illustrates an example of displaying annotated image sequence with thumbnail images according to the present invention, where a pointer can be moved around a timeline to select an image to be displayed.

After a corresponding annotated image is displayed, the viewer may desire to examine images around the annotated image. Navigation through the image sequence can be accomplished by indication through the user interface. For example, a user may use a pointing device such as a computer mouse to "drag" pointer 310A to a desirable location as shown in FIG. 3A. When a navigation bar (140) is used, a pointer corresponding to a currently displayed image can be used so that a user may drag the pointer (310A) to navigate through the image sequence. When the pointer (310A) is dragged along the navigation bar and moves pass an annotated image, it will be useful that a visual alert is generated to indicate the case. Accordingly, an embodiment of the present invention changes the display of the corresponding thumbnail image when the pointer is moving pass the annotated image associated with the thumbnail image. Changing the display of the corresponding thumbnail image may correspond to highlighting the thumbnail image by adding a surrounding box or overlaying with solid/partially transparent graphic, replacing the thumbnail image with symbol/token, or blanking out the thumbnail image. After the pointer moves away from the annotated image, the display of the corresponding thumbnail image may resume.

Figure 3B:
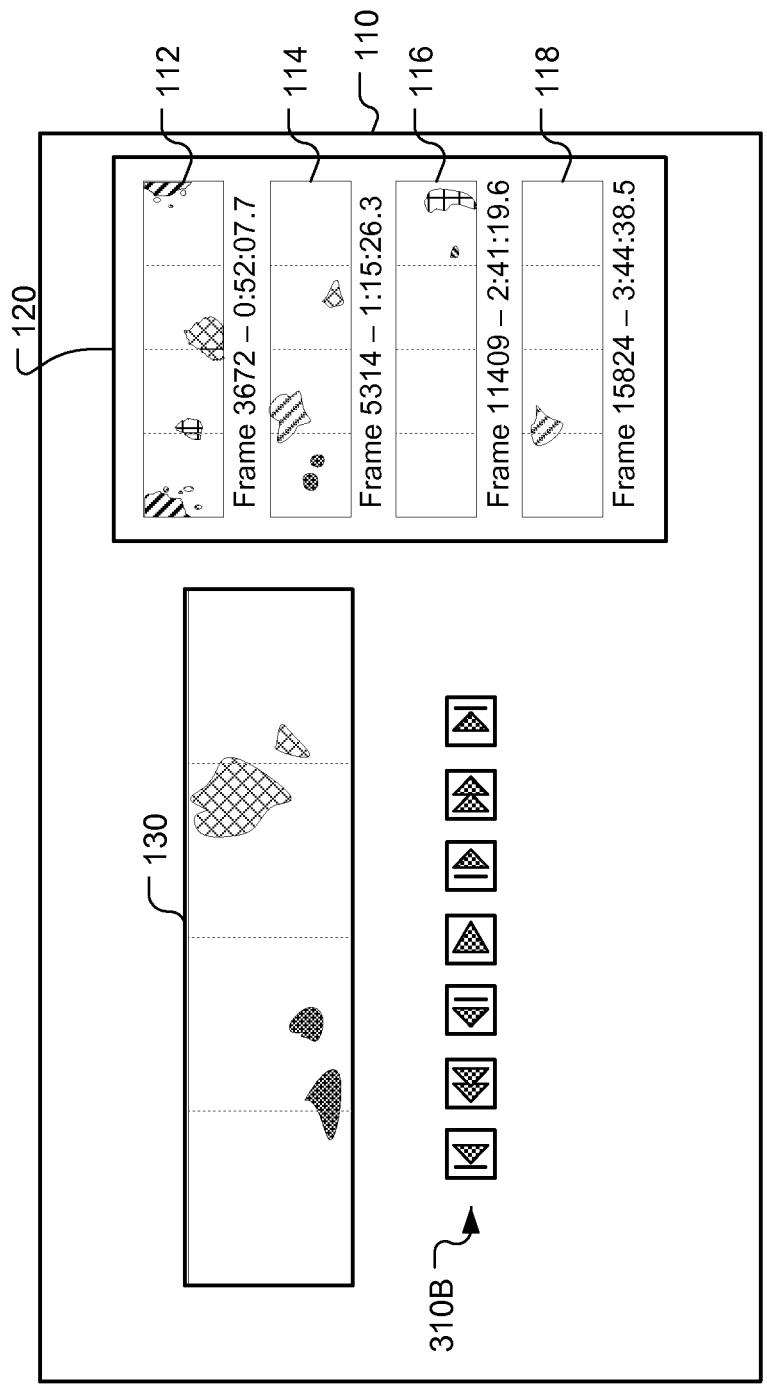
FIG. 3B illustrates an example of displaying annotated image sequence with thumbnail images according to the present invention, where a playback control is used to navigate through the sequence.

As mentioned before, navigation bar 140 is optional. The current invention is also applicable to a display system without the navigation bar. For example, a display system incorporating an embodiment of the present invention may use simple display control such as Play/Pause, Next Frame, Previous Frame, Fast Forward, Reverse, Move-to-Beginning and Move-to-End. Alternatively, graphic user interface (GUI) 310B can be displayed to allow actions such as Play/Pause, Next Frame, Previous Frame, Fast Forward, Reverse, Move-to-Beginning and Move-to-End as shown in FIG. 3B. When an annotated image in the image sequence is displayed, the corresponding thumbnail image is changed to indicate the occurring correspondence between a currently displayed annotated image and a thumbnail image. While FIG. 3A and FIG. 3B illustrate examples of navigation bar and GUI based control to navigate through the image sequence, a system may also use a computer keyboard or dedicated buttons to navigate through the image sequence. In this case, a desired playback action may be achieved by pressing one or more keys or button. A viewer may use the playback control to pause at an image of interest or to step through a neighborhood of a selected image. Viewing the image sequence using Pause, Next Frame, Previous Frame, Go-To-Frame, or other similar control will allow a user to closely examine a selected frame. Accordingly, any of these modes that allow a user to examine a selected frame is referred to as Single Frame mode in this disclosure. When the display is paused at an annotated image or a frame is advanced to an annotated image, it is useful to alert the viewer that the currently display image is an annotated image and there is a correspondence between the annotated image and a thumbnail image. An embodiment of the present invention changes the display of the corresponding thumbnail image to indicate the occurring correspondence and causes a visual alert. The techniques described above associated with FIG. 2A through FIG. 2D can be applied to cause the visual alert to indicate the occurring correspondence.

Figure 4A:
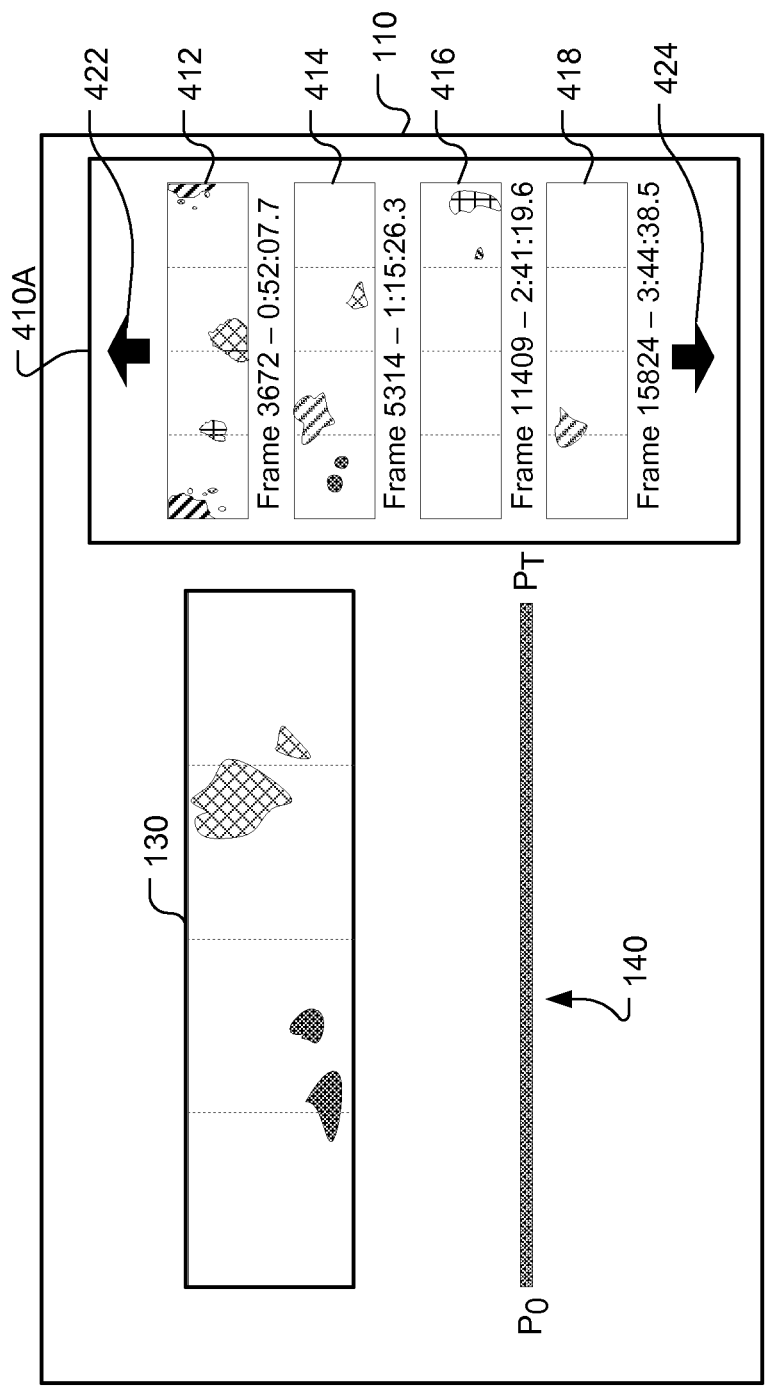
FIG. 4A illustrates an example of displaying annotated image sequence with thumbnail images according to the present invention, where user interface is provided to allow a user to select a subset of thumbnail images corresponding to different annotated images displayed.
Figure 4B:
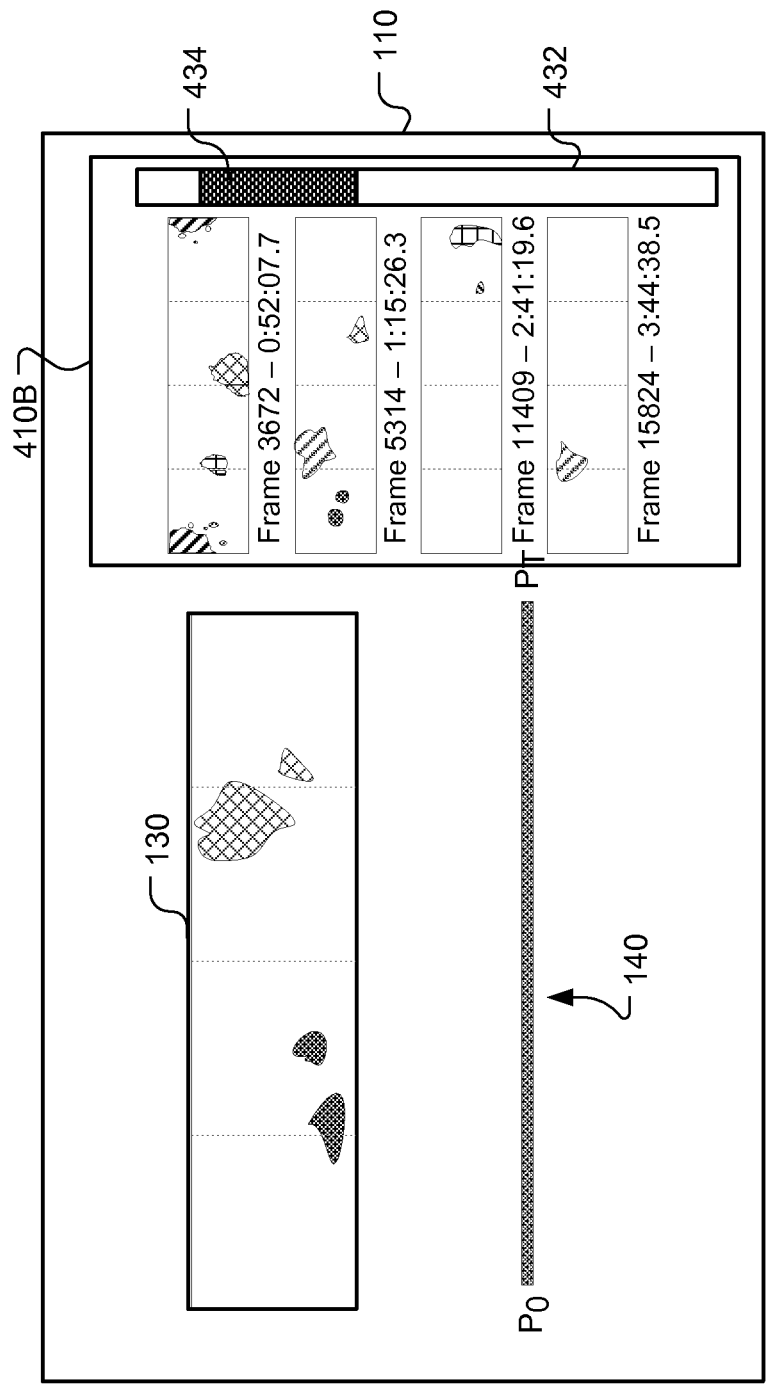
FIG. 4B illustrates another example of displaying annotated image sequence with thumbnail images according to the present invention, where user interface is provided to allow a user to select a subset of thumbnail images corresponding to different annotated images displayed.

The number of annotated images may be large and the associated thumbnail images may not fit into the display area designated for the thumbnail images. Another embodiment according to the present invention displays a subset of the thumbnail images in the display area and provides a user interface to allow a user to select a different subset to be displayed in the thumbnail display area. FIG. 4A illustrates an example where thumbnail image 412 through 418 are displayed in thumbnail display area 420 designated for thumbnail images. Arrows 422 and 424 are provided to allow the user to scroll through thumbnail images and to cause other thumbnail images displayed in display area 410A. As shown in the timeline 140 of FIG. 4A, there are more annotated images as marked on the navigation bar. FIG. 4B illustrates an alternative graphic user interface to allow a user to scroll around the thumbnail images. In FIG. 4B, slide 434 can be moved up and down within a selection range 432 to select a range of thumbnail images to be displayed in display area 410B. Slide 434 may be controlled using a pointing device such as a computer mouse through a cursor displayed on the display device.

Figure 5A:
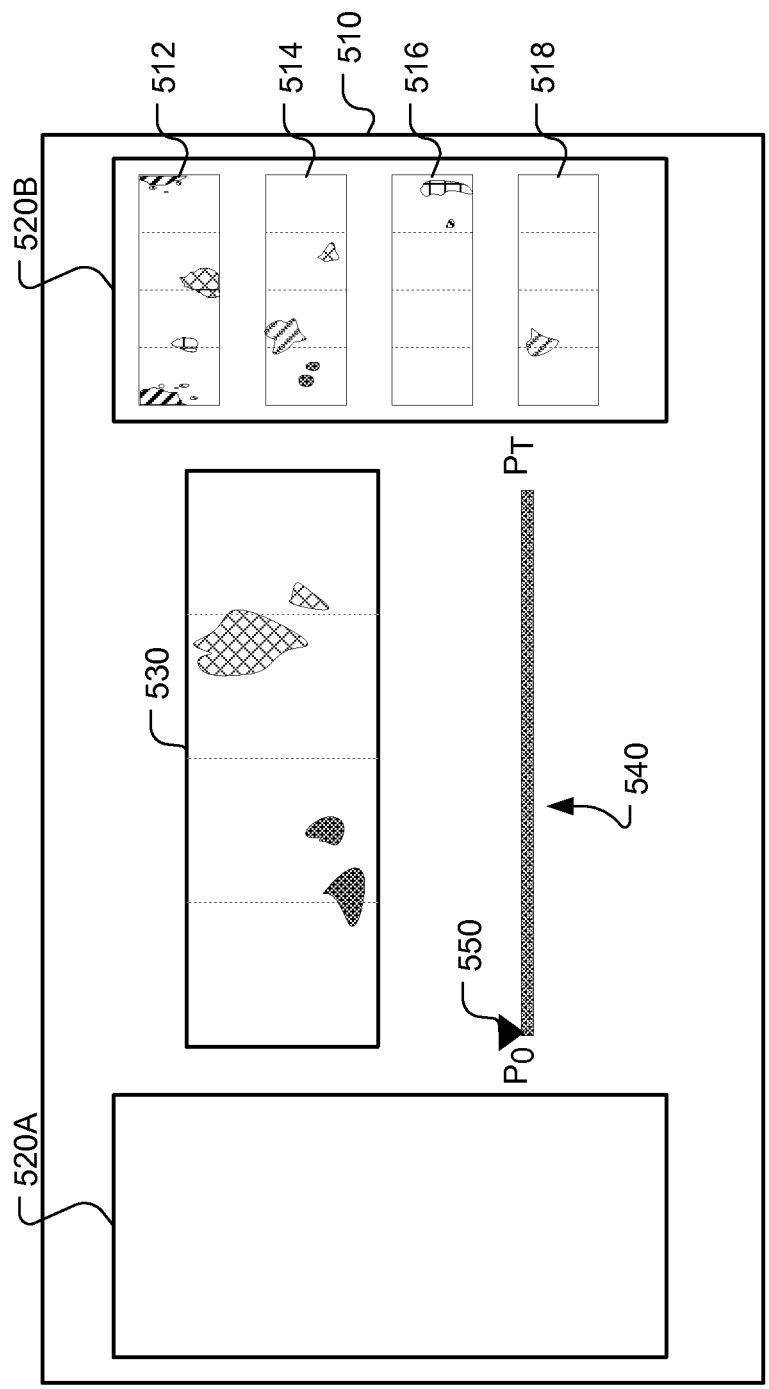
FIGS. 5A-C illustrate an example of displaying annotated image sequence with thumbnail images according to the present invention, where two sets of thumbnail images correspond to annotated images located before and after a currently displayed image respectively.
Figure 5B:
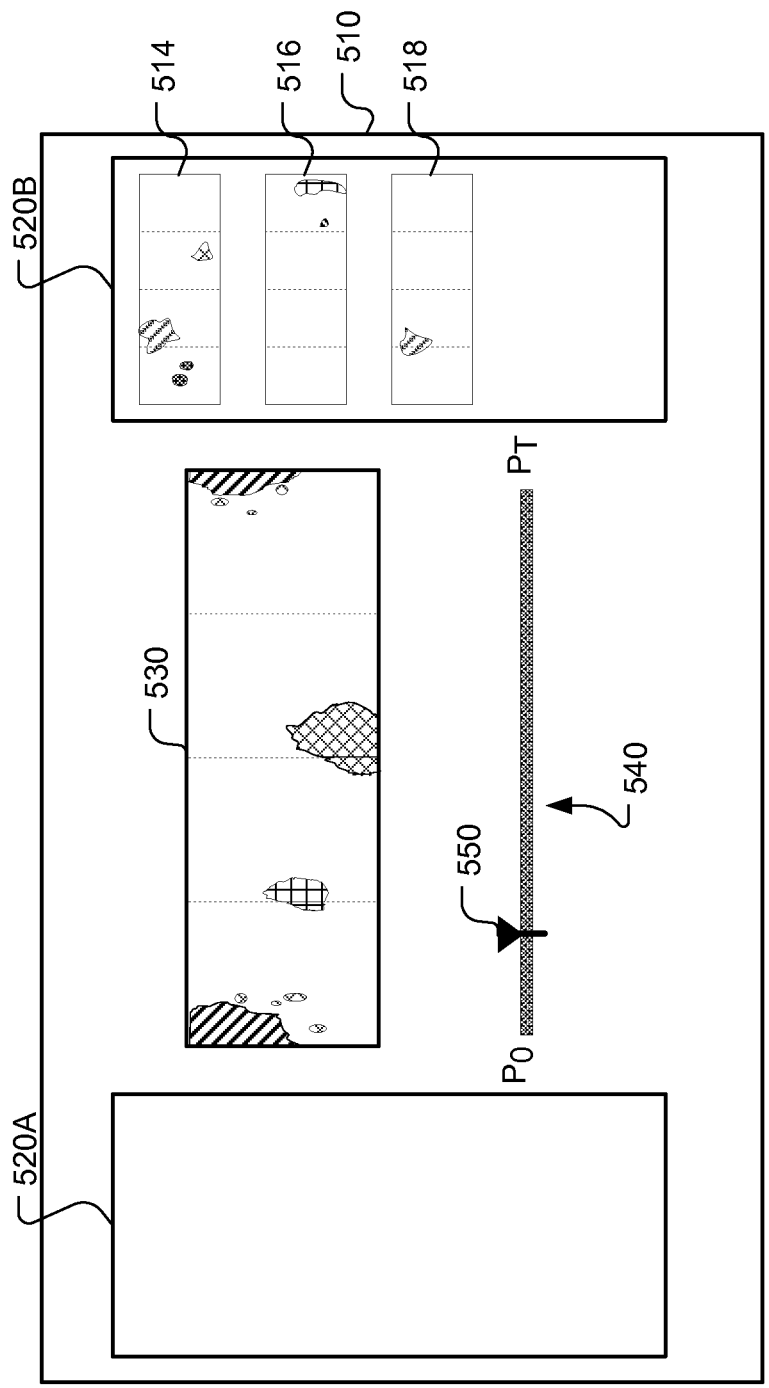
Figure 5C:
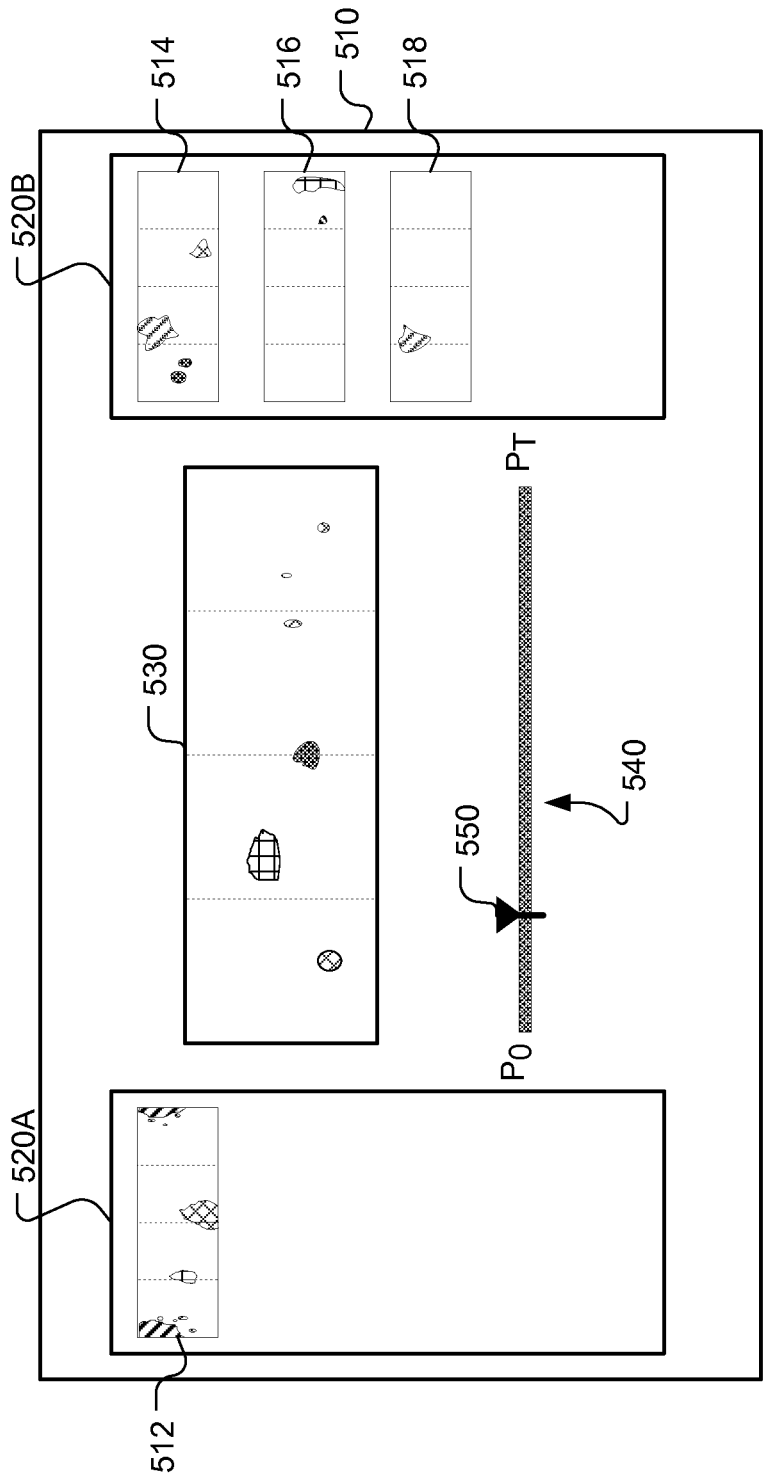

As describe above, the occurring correspondence between an annotated image being displayed and a corresponding thumbnail image can be indicated by changing the display of the corresponding thumbnail image. In another embodiment of the present invention, two thumbnail display areas are used to facilitate the indication of occurring correspondence between an annotated image being displayed and a corresponding thumbnail image as shown in FIG. 5A and FIG. 5B. Two thumbnail display areas 520A and 520B are provided on the screen of display device 510. Display area 530 is used to display the image sequence. One of the thumbnail display areas is used for thumbnail images before the currently displayed image and the other is used for thumbnail images after the currently displayed image. For example, thumbnail display area 520A is used for thumbnail images before the currently displayed image and thumbnail display area 520B is used for thumbnail images after the currently displayed image as shown in FIG. 5A. FIG. 5A illustrates the example that the first image in the sequence is being displayed. Therefore, there is no thumbnail image in thumbnail display area 520A and all thumbnail images (512-518) are in thumbnail display area 520B. If the thumbnail display area cannot accommodate all the thumbnail images at the same time, thumbnail image scrolling as shown in FIG. 4A and FIG. 4B can be used. When the currently displayed image corresponds to an annotated image, the corresponding thumbnail image will be blanked out from the original thumbnail display area. FIG. 5B illustrates and example that an annotated image having corresponding thumbnail image 512 is displayed in display area 530. Thumbnail image 512 is blanked out from display area 520B. After display of the annotated image is finished, the corresponding thumbnail image will be displayed in the other thumbnail display area. FIG. 5C illustrates an example that thumbnail image 512 is displayed in the other thumbnail display area (i.e., 520A) after display of the corresponding annotated image is finished. In other words, the occurring correspondence between an annotated image and a thumbnail image corresponding to the annotated image is indicated by moving the corresponding thumbnail image from one display area to the other. An optional navigation bar is also shown in FIG. 5A-FIG. 5C.

Figure 6A:
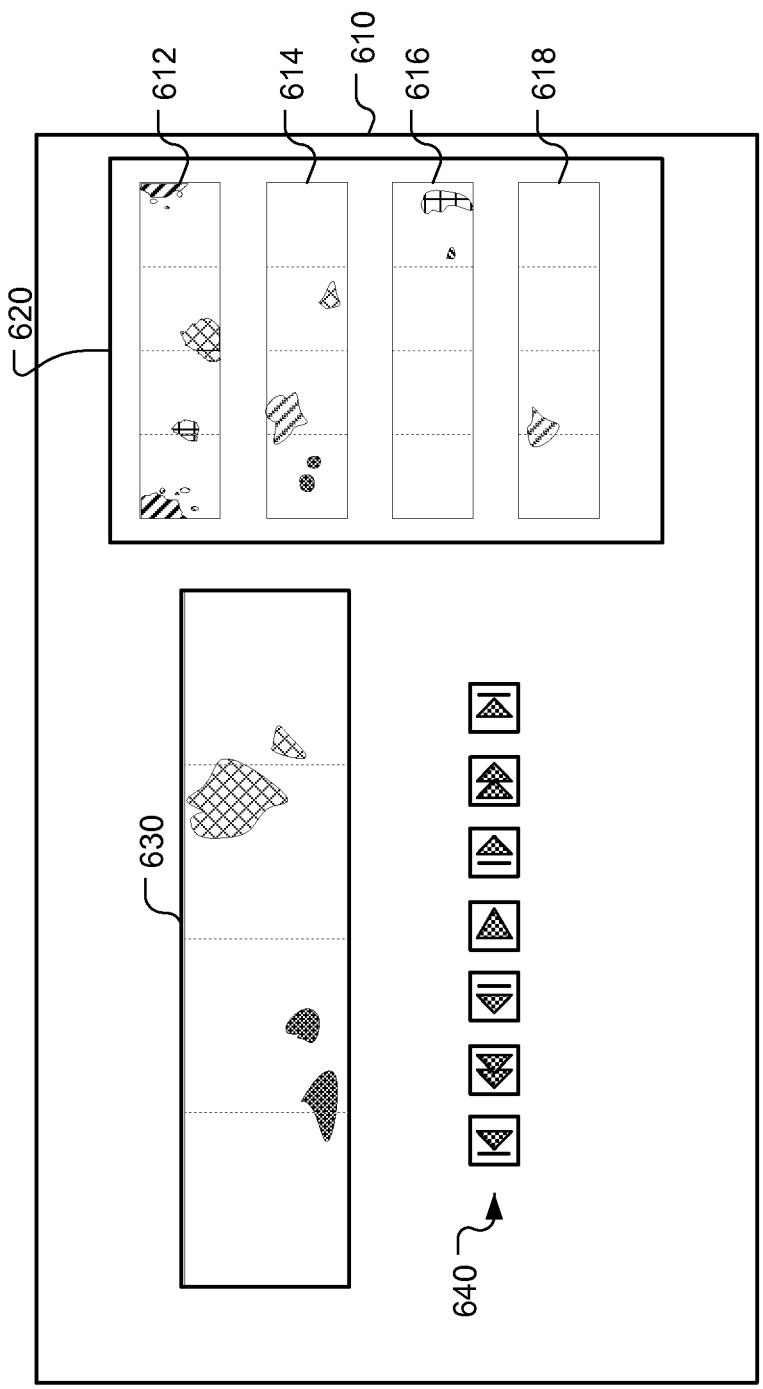
FIGS. 6A-B illustrate an example of displaying annotated image sequence with thumbnail images according to the present invention, where the main display area is increased by hiding the display area for thumbnail images during Play mode.
Figure 6B:
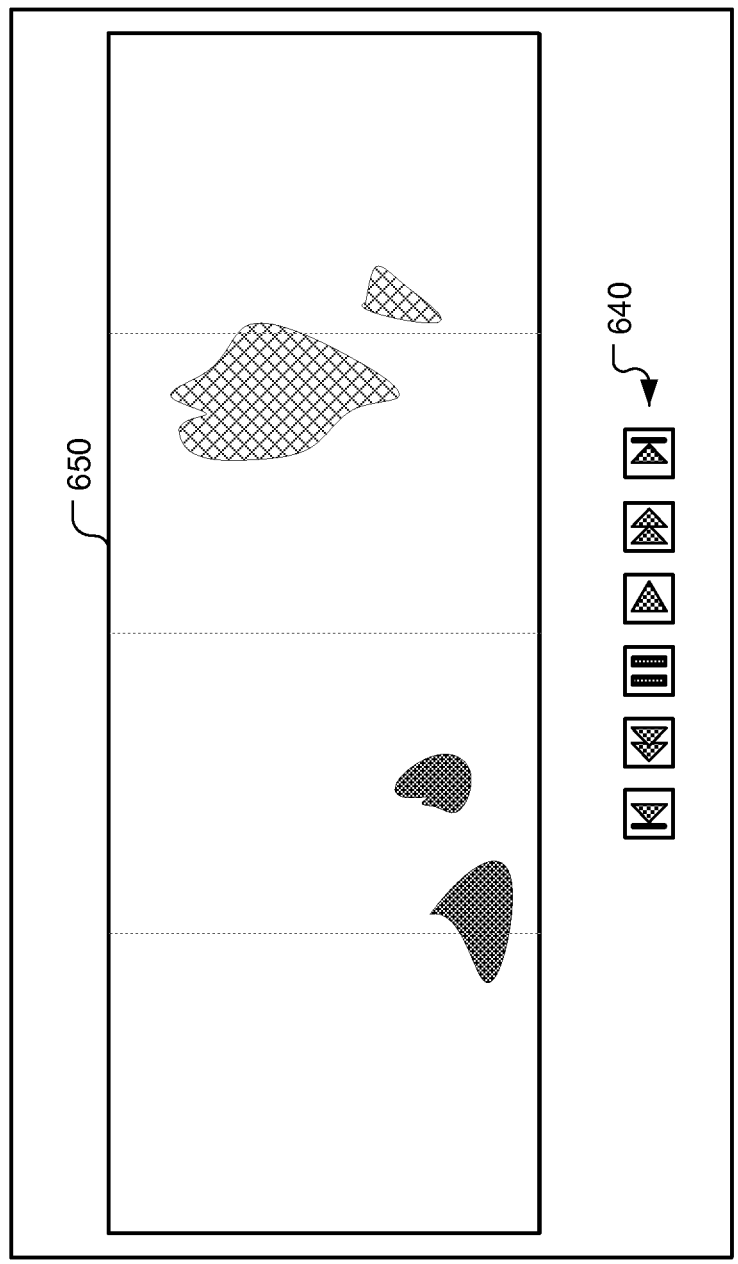

The concurrent display of image sequence in a main display area and thumbnail images/annotations in a second display area is useful for a doctor or medical professional to quickly locate points of interest in the image sequence. However, some doctors/medical professionals may prefer to maximize the main display area during sequence play so that it is easier to see detail contents in the image sequence. FIG. 6A and FIG. 6B illustrate an example of maximizing mail display area during sequence play mode. FIG. 6A illustrate a scenario where, on the screen of display device 610, the thumbnail images 612-618 are displayed in thumbnail display area 620 along with an image in the image sequence displayed in main display area 630. The scenario may correspond to sequence pause (Pause mode) or frame stepping (Frame mode) that allows a viewer to examine the image in the main display area closely. After the detailed examination, the viewer may continue to identify other anomaly or points of interest in the image sequence by entering Play mode. FIG. 6B illustrates an example of increased main display area 650 for viewing images at a larger size during Play mode. As shown in FIG. 6B, the main display area is increased by eliminating the thumbnail display area. The viewer may signal an indication to the system regarding viewer's desire to switch to the Pause or Frame mode. The viewer's input may be provided using a computer keyboard/mouse or a dedicated input device with buttons, joystick, pointing device or a combination thereof. Alternatively, a graphic user interface (GUI, 640) may be displayed to allow a viewer to control playback using a pointing device such as a computer mouse with buttons. The pointing device along with a cursor displayed on screen allows a user to select one of the playback control buttons.

Figure 7A:
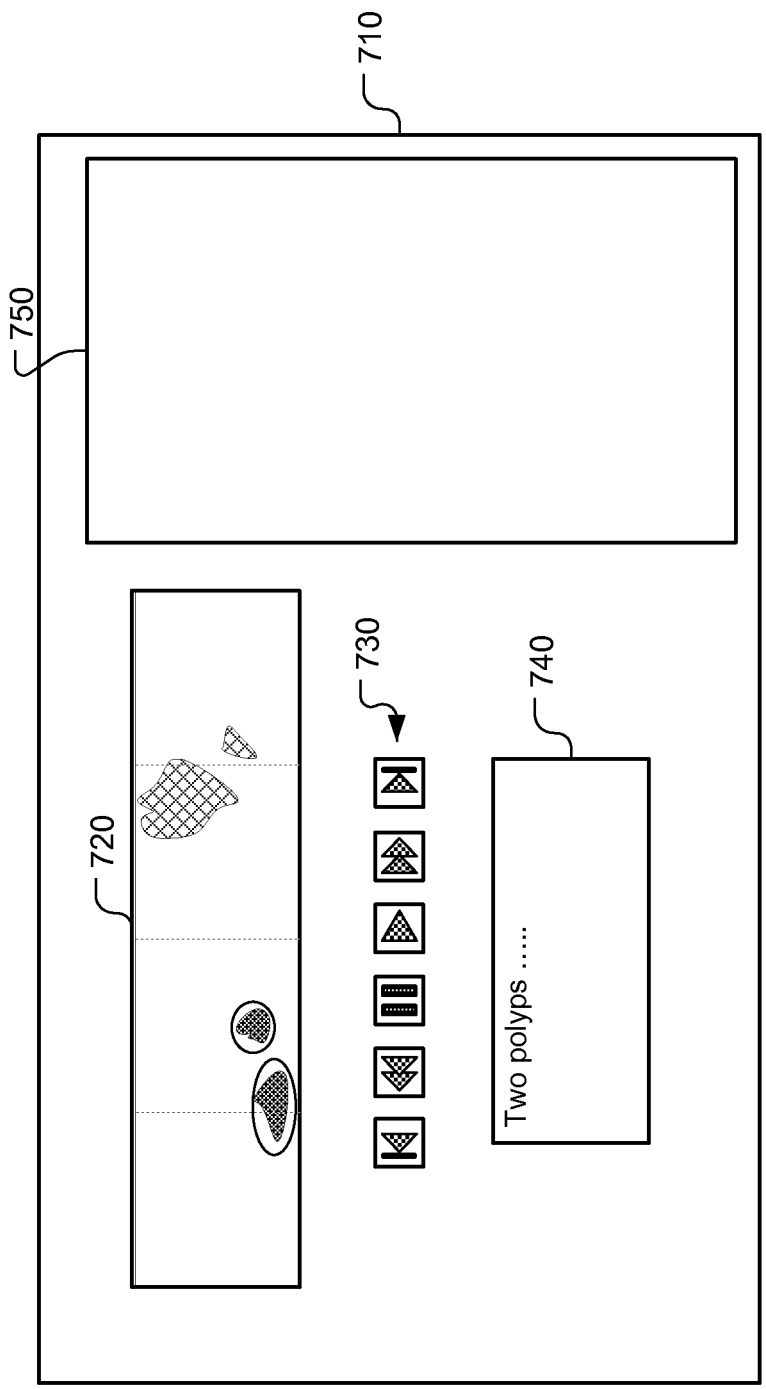
FIG. 7A illustrates an example of an annotation/thumbnail image creation in the initial state according to the present invention.
Figure 7B:
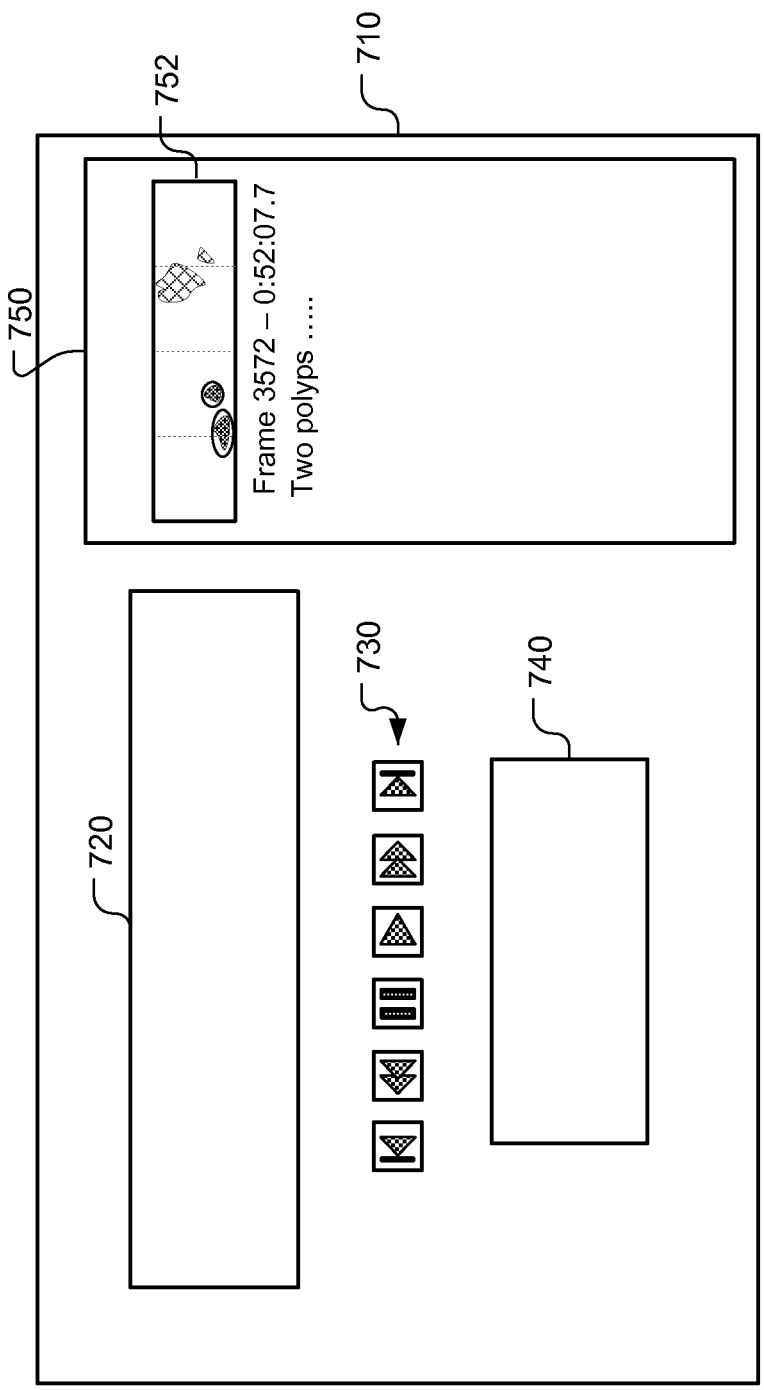
FIG. 7B illustrates an example of an annotation/thumbnail image creation according to the present invention, where an annotated image is done.

Annotation and thumbnail images can be created during image sequence viewing. Initially, the annotation and thumbnail images may be empty. The display arrangement for annotation/thumbnail image generation is similar to that for playback. However, an area for typing/displaying annotation text is needed. FIG. 7A illustrates an example of display arrangement for annotation/thumbnail image creation. Display area 720, playback control 730, annotation area 740 and thumbnail display area 750 are shown on the screen of display device 710. A viewer may play the image sequence using playback control 730 to locate a picture of interest. When an image to be annotated is located, annotation tools such as text inputting/editing (either on the image or in annotation text box 740) and graphic on image can be used to add annotation. When annotation is done with a selected image, the annotation information along with a thumbnail image can be saved with files associated with the image sequence data or saved as a separate file/database. When the annotation is done with a selected image, the corresponding thumbnail image can be displayed in thumbnail display area 750. At the same time, the annotated image is blanked out from display area 720 to indicate annotation of the currently image has been accepted and/or stored. The system is now ready for annotation of another image. The doctor may also continue to view the image sequence without adding any annotated image. During annotating, the doctor also has the need to view the annotated image sequence, which may be partially annotated or not annotated (before a first image is annotated). Accordingly, the annotating process may be considered as an additional feature to displaying annotated images.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

An embodiment of the present invention to perform the steps disclosed in this application can be based on an application specific integrated circuit (ASIC), a microcontroller, or a hardware-based processor. An embodiment of the present invention may also be program codes to be executed on a Digital Signal Processor (DSP) to perform the processing described herein. The invention may also involve a number of functions to be performed by a computer processor, a digital signal processor, a microprocessor, or field programmable gate array (FPGA). These processors can be configured to perform particular tasks according to the invention, by executing machine-readable software code or firmware code that defines the particular methods embodied by the invention. The software code or firmware codes may be developed in different programming languages and different format or style. The software code may also be compiled for different target platform. However, different code formats, styles and languages of software codes and other means of configuring code to perform the tasks in accordance with the invention will not depart from the spirit and scope of the invention.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for displaying images captured by an in vivo imaging device on a display device, the method comprising:
   receiving image sequence data captured with the in vivo imaging device for a body lumen, wherein the image sequence data includes one or more annotated images;
   displaying the image sequence data in a first display area as a video;
   if none of the annotated images corresponding to one or more thumbnail images is being displayed in the first display area, displaying said one or more thumbnail images in a second display area, wherein said one or more thumbnail images correspond to said one or more annotated images of the image sequence data; and
   if a first annotated image corresponding to a first thumbnail image is displayed in the first display area, displaying said one or more thumbnail images by changing the first thumbnail image in the second display area to indicate an occurring correspondence between the first annotated image and the first thumbnail image corresponding to the first annotated image being displayed.

2. The method of claim 1, further comprising displaying the first thumbnail image in the second display area when one other image of the image sequence data is displayed in the first display area after the first annotated image finishes displaying.

3. The method of claim 1, further comprising displaying annotation information associated with the annotated images.

4. The method of claim 1, further comprising displaying a timeline associated with the image sequence data, wherein markers are shown on the timeline to indicate locations of the annotated images.

5. The method of claim 1, wherein said changing the first thumbnail image in the second display area corresponds to replacing the first thumbnail image with a blank space.

6. The method of claim 1, wherein said changing the first thumbnail image in the second display area corresponds to replacing the first thumbnail image with a token or text information.

7. The method of claim 6, wherein the token corresponds to image information associated with the first annotated image being displayed.

8. The method of claim 7, wherein the image information corresponds to annotation information, frame information, time information, or any combination thereof.

9. The method of claim 6, wherein the token corresponds to a representative icon.

10. The method of claim 1, wherein said changing the first thumbnail image in the second display area corresponds to highlighting the first thumbnail image.

11. The method of claim 10, wherein said highlighting the first thumbnail image corresponds to adding an outline box or a graphic overlay with solid color or partial opacity.

12. The method of claim 1, wherein said changing the first thumbnail image in the second display area lasts longer than one frame period.

13. The method of claim 1, wherein the thumbnail images are associated with a first set of thumbnail images and a second set of thumbnail images, wherein at least one attribute for the first set of thumbnail images and the second set of thumbnail images is different.

14. The method of claim 13, wherein the second display area comprises a third display area and a fourth display area, the first set of thumbnail images are displayed in the third display area and the second set of thumbnail images are displayed in the fourth display area.

15. A method for displaying images captured by an in vivo imaging device on a display device, the method comprising:
   receiving image sequence data captured with the in vivo imaging device for a body lumen, wherein the image sequence data includes one or more annotated images;
   displaying a current image of the image sequence data in a first display area, wherein said displaying the current image is caused by pausing display of the image sequence data or frame stepping through the image sequence data;
   if the current image being displayed in the first display area does not correspond to any annotated image, displaying one or more thumbnail images in a second display area, wherein said one or more thumbnail images correspond to said one or more annotated images of the image sequence data; and
   if the current image corresponds to a first annotated image, displaying said one or more thumbnail images by replacing a first thumbnail image in the second display area corresponding to the first annotated image to indicate an occurring correspondence between the first annotated image and the first thumbnail image.

16. The method of claim 15, wherein said replacing the first thumbnail image in the second display area corresponds to replacing the first thumbnail image with a blank space, another thumbnail image or a token.

17. A method for displaying images captured by an in vivo imaging device on a display device, the method comprising:
   receiving image sequence data captured with the in vivo imaging device for a body lumen, wherein the image sequence data includes one or more annotated images;
   displaying a navigation bar with a location marker to indicate locations associated with images of the image sequence data;
   displaying a current image of the image sequence data in a first display area as indicated by the location marker; and displaying thumbnail images depending on the location marker, wherein the thumbnail images correspond to annotated images of the image sequence data, wherein said displaying the thumbnail images corresponds to displaying one or more thumbnail images in a second display area if the location marker does not point to any annotated image, and said displaying the thumbnail images corresponds to displaying said one or more thumbnail images by changing or highlighting a first thumbnail image in the second display area if the location marker is moved pass a first location corresponding to a first annotated image corresponding to the first thumbnail image to indicate an occurring correspondence between the first annotated image and the first thumbnail image.

18. The method of claim 17, wherein said changing or highlighting the first thumbnail image in the second display area corresponds to replacing the first thumbnail image with a blank space, another thumbnail image or a token.

19. A method for displaying images captured by an in vivo imaging device on a display device, the method comprising:
receiving image sequence data captured with the in vivo imaging device for a body lumen;
displaying the image sequence data in a first display area as a video;
displaying a first set of one or more thumbnail images in a second display area, wherein the first set of one or more thumbnail images corresponding to annotated images of the image sequence data located before a current image being displayed;
displaying a second set of one or more thumbnail images in a third display area, wherein of the second set of one or more thumbnail images corresponding to the annotated images of the image sequence data located after the current image being displayed; and
if the current image being displayed corresponds to a first annotated image, removing a first thumbnail image corresponding to the first annotated image from the first set of one or more thumbnail images to the second set of one or more thumbnail images.

20. The method of claim 19, wherein the first thumbnail image in the second display area is changed by replacing with a blank space, another thumbnail image or a token.

21. A system for displaying capsule images, the system comprising:
a display device; and
a controller configured to:
receive image sequence data captured with an in vivo imaging device for a body lumen, wherein the image sequence data includes one or more annotated images;
display the image sequence data in a first display area as a video;
if none of annotated images corresponding to one or more thumbnail images is being displayed in the first display area, display said one or more thumbnail images in a second display area on the display device, wherein said one or more thumbnail images correspond to one or more annotated images of the image sequence data; and
if a first annotated image corresponding to a first thumbnail image is displayed in the first display area, display said one or more thumbnail images by changing the first thumbnail image in the second display area to indicate an occurring correspondence between the first annotated image and the first thumbnail image corresponding to the first annotated image being displayed.

22. The system of claim 21, the controller is further configured to display the first thumbnail image in the second display area when one other image of the image sequence data is displayed in the first display area after the first annotated image finishes displaying.

23. The system of claim 21, the controller is further configured to display annotation information associated with the annotated images.

24. The system of claim 21, the controller is further configured to display a timeline associated with the image sequence data, wherein markers are shown on the timeline to indicate locations of the annotated images.

25. The system of claim 21, wherein the first thumbnail image in the second display area is replaced by a blank space or another thumbnail image.

26. The system of claim 21, wherein the first thumbnail image in the second display area is replaced by a token.

27. The system of claim 21, wherein first thumbnail image in the second display area is replaced for more than one frame period.

28. A method for annotating images captured with an in vivo imaging device, the method comprising:
receiving image sequence data captured with the in vivo imaging device for a body lumen;
displaying the image sequence data in a first display area;
selecting one image to be annotated from the image sequence data;
accepting annotation information from a user for said one image to generate one annotated image;
generating a thumbnail images corresponding to said one annotated image;
displaying the thumbnail image corresponding to said one annotated image in a second display area and blanking out said one annotated image from the first display area as a confirmation for the thumbnail image generated; and
storing the annotation information in a file or a database.

29. The method of claim 28, wherein annotation information comprises text, graphics, or both.

30. The method of claim 28, further comprising providing user interface for entering/editing text, applying graphics on the annotated images, or both.

* * * * *